(12) United States Patent
Jordan

(10) Patent No.: US 6,950,697 B2
(45) Date of Patent: Sep. 27, 2005

(54) ELECTROENCEPHALOGRAM ACQUISITION UNIT AND SYSTEM

(75) Inventor: Kenneth George Jordan, Riverside, CA (US)

(73) Assignee: Jordan Neuroscience, Inc., San Bernardino, CA (US)

( * ) Notice: Subject to any disclaimer, the term of this patent is extended or adjusted under 35 U.S.C. 154(b) by 62 days.

(21) Appl. No.: 10/065,306

(22) Filed: Oct. 1, 2002

(65) Prior Publication Data

US 2003/0018278 A1 Jan. 23, 2003

Related U.S. Application Data

(62) Division of application No. 09/756,417, filed on Jan. 8, 2001, now Pat. No. 6,510,340.
(60) Provisional application No. 60/175,191, filed on Jan. 10, 2000, provisional application No. 60/175,192, filed on Jan. 10, 2000, and provisional application No. 60/175,193, filed on Jan. 10, 2000.

(51) Int. Cl.$^7$ .............................. A61B 5/04; A61B 5/00; A61B 10/00; G06F 17/30
(52) U.S. Cl. ....................... 600/544; 600/300; 128/920; 707/9; 707/1
(58) Field of Search ................................ 600/544, 545, 600/300, 897, 898; 128/920, 923–925; 705/1–3; 707/1, 9, 10

(56) References Cited

U.S. PATENT DOCUMENTS

| | | | |
|---|---|---|---|
| 3,735,753 A | 5/1973 | Pisarski | 128/2.1 E |
| 3,951,134 A | 4/1976 | Malech | 128/2.1 B |
| 3,998,213 A | 12/1976 | Price | 128/2.1 B |
| 4,537,198 A | 8/1985 | Corbett | 128/639 |
| 4,566,464 A | 1/1986 | Piccone et al. | 128/732 |
| 4,838,275 A | 6/1989 | Lee | 128/670 |
| 4,928,696 A | 5/1990 | Henderson et al. | 128/644 |
| 5,038,782 A | 8/1991 | Gevins et al. | 128/644 |
| 5,291,888 A | 3/1994 | Tucker | 128/644 |
| 5,293,867 A | 3/1994 | Oommen | 128/630 |
| 5,357,957 A | 10/1994 | Itil et al. | 128/644 |
| 5,421,343 A * | 6/1995 | Feng | 600/523 |
| 5,479,934 A | 1/1996 | Imran | 128/731 |
| 5,518,007 A | 5/1996 | Becker | 128/774 |
| 5,544,649 A | 8/1996 | David et al. | 128/630 |
| 5,626,145 A | 5/1997 | Clapp et al. | 128/731 |
| 5,730,146 A | 3/1998 | Itil et al. | 128/732 |
| 5,791,342 A | 8/1998 | Woodard | 128/630 |
| 5,800,351 A | 9/1998 | Mann | 600/383 |
| 5,807,270 A | 9/1998 | Williams | 600/547 |
| 5,817,029 A | 10/1998 | Gevins et al. | 600/544 |
| 5,857,978 A | 1/1999 | Hively et al. | 600/544 |
| 5,862,803 A | 1/1999 | Besson et al. | 128/696 |
| 5,931,791 A | 8/1999 | Saltzstein et al. | 600/513 |
| 5,941,829 A | 8/1999 | Saltzstein et al. | 600/509 |

(Continued)

OTHER PUBLICATIONS

Vaidyanathan, et al., "A Sampling Theorem for EEG Electrode Configuration", IEE Transactions on Biomedical Engineering, vol. 44, No. 1, Jan. 1997, pp 94–97.

Primary Examiner—Robert L. Nasser
Assistant Examiner—Navin Natnithithadha
(74) Attorney, Agent, or Firm—Sheldon & Mak; Robert J. Rose; Michael Fedrick

(57) ABSTRACT

An acquisition unit provided which provides a turn-key interface to the non-expert personnel who attend acutely brain-injured victims, preventing change or modification of the electroencephalogram parameters by the field technician, while at the same time allowing extensive control over parameters by a remote expert EEG reader; and a method and system is provided using the template and acquisition unit of the present invention with one of a plurality of remote readers who are part of a network of trained EEG readers.

15 Claims, 12 Drawing Sheets

U.S. PATENT DOCUMENTS

| | | | |
|---|---|---|---|
| 5,957,854 A | 9/1999 | Besson et al. | 600/509 |
| 5,961,446 A | 10/1999 | Beller et al. | 600/300 |
| 5,975,081 A | 11/1999 | Hood et al. | 128/845 |
| 6,011,991 A | 1/2000 | Mardirossian | 600/544 |
| 6,052,619 A | 4/2000 | John | 600/544 |
| 6,115,623 A | 9/2000 | McFee | 600/372 |
| 6,128,521 A | 10/2000 | Marro et al. | 600/383 |
| 6,161,030 A | 12/2000 | Levendowski et al. | 600/383 |
| 6,234,964 B1 * | 5/2001 | Iliff | 600/300 |
| 6,416,471 B1 * | 7/2002 | Kumar et al. | 600/300 |
| 6,510,340 B1 * | 1/2003 | Jordan | 600/544 |
| 6,697,894 B1 * | 2/2004 | Mitchell et al. | 710/73 |

* cited by examiner

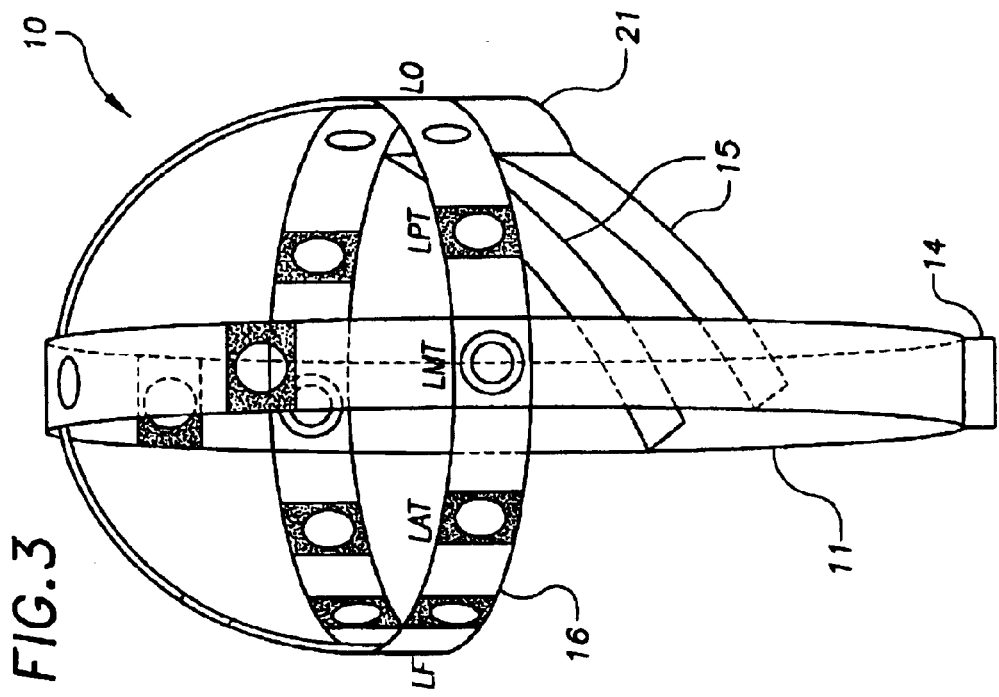
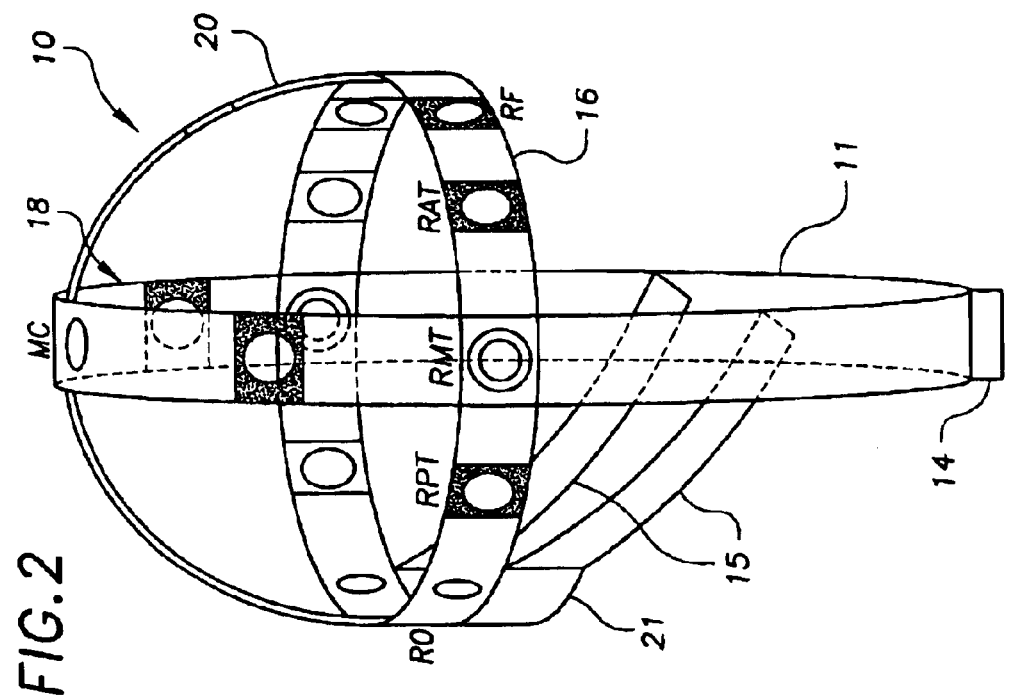

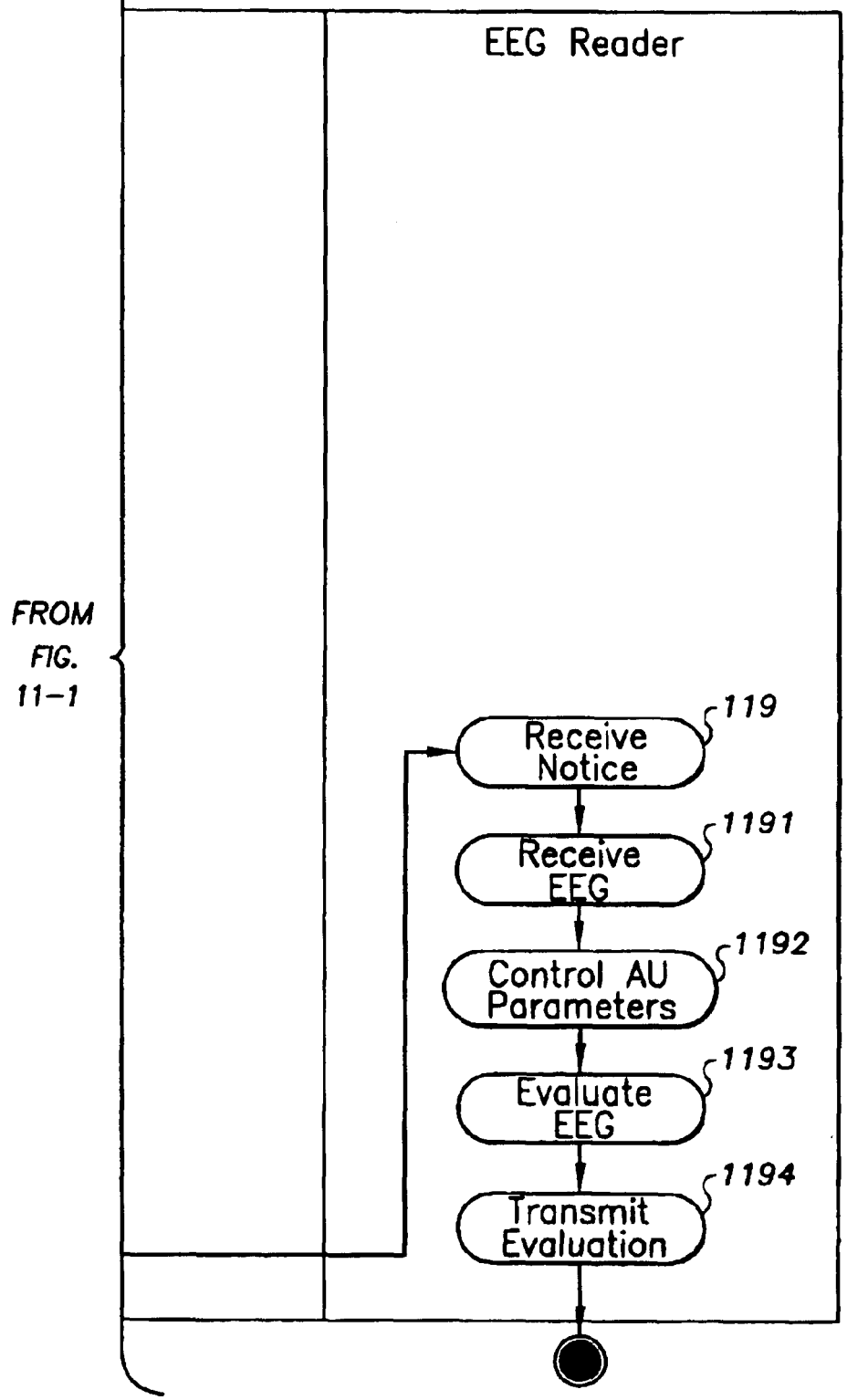

ELECTROENCEPHALOGRAM ACQUISITION UNIT AND SYSTEM

CROSS REFERENCE TO RELATED APPLICATIONS

This application is a division of U.S. patent application Ser. No. 09/756,417 filed Jan. 8, 2001 now U.S. Pat. No. 6,510,340, titled "Method And Apparatus For Electroencephalography" and claims priority from provisional applications Ser. No. 60/175,191, filed Jan. 10, 2000; Ser. No. 60/175,192, filed Jan. 10, 2000; and Ser. No. 60/175,193, filed Jan. 10, 2000.

BACKGROUND OF INVENTION

A variety of acute brain injuries occur in patients presenting to emergency rooms.

These injuries include acute strokes, seizures, head trauma, and sudden changes of consciousness. In 1996, there were 97 million emergency room visits in the United States alone. Of these visits, it is conservatively estimated that at least seven to eight percent, or between 6.8 and 7.8 million people suffered acute brain dysfunction.

Despite these numbers, electroencephalography (EEG), a standard, noninvasive test to evaluate brain function, is not available or rarely performed in emergency departments in the United States. Many emergency departments affiliated with major academic centers never perform emergency room electroencephalography (ER-EEG) on patients with acute brain problems. Few of these institutions even have ER-EEG regularly available, and then only perform 2–3 per month. This presents a serious unmet medical need.

In the last several years, fundamental changes have occurred in the medical community's approach to acute brain injuries and in EEG technology. These changes make provision of ER-EEG critically important to the health care industry.

As an example, acute strokes are now considered medical emergencies. Effective "clot busting" (thrombolytic) therapy, previously used only for heart attacks, is now able to minimize brain damage, but only within a three-hour time window from the onset of the stroke. This time urgency has moved acute stroke from a previously untreatable disorder to a "brain attack," equivalent in its urgency to heart attack and head trauma. This brain attack paradigm applies to all patients with acute brain injuries, including head trauma, brain hemorrhage, seizures, or acute altered consciousness. The clock for brain survival starts ticking at the onset of the injury and runs out quickly. We now know that rapid and accurate diagnosis and treatment of acute brain injuries determines outcome. Acutely brain-injured patients' survival and quality of survival depend on rapid and accurate diagnosis of their specific brain injuries.

The EEG is known to provide important electrophysiological data about brain function analogous to the electrocardiogram ("EKG") in acute cardiac injury. The EEG can identify structural, metabolic, seizure, anoxic, and progressive brain abnormalities in the acute setting. This crucial information about brain function in acute brain injuries is currently not obtainable until after patients are admitted to the hospital, which can mean many hours and even days for the brain injury to worsen, often causing irreversible damage by the time it is identified. Further contributing to delay, specialized personnel are needed to administer EEG, and the experts needed to interpret ER-EEGs may be far removed from the emergency department.

The International 10-20 System ("10-20 System") is a well-known method used to locate scalp electrodes for EEG readings, based on the relationship between the location of an electrode and the underlying area of the cerebral cortex. The 10-20 System teaches the use of a large number of electrodes, requiring either 19 or 21 electrodes, including one electrode position which acts as a ground. Such large number of electrode positions are necessary when taking EEGs for reference against prior standard tests or EECs, but it may not be necessary for specialized needs. For example, U.S. Pat. No. 6,052,619 to John discloses the use of 2 to 16 EEG electrodes in field emergency situations. When using a reduced number of electrodes, however, there is a trade-off between the time saved in placement of the electrodes and the quality of EEG information produced. Fewer electrodes results In longer interApp electrode distances, with greater risk of noise in the reading. It is possible that modification of electrode locations from that taught by the standard 10-20 System, in particular moving the location of the ground electrode closer to one or more active electrodes, might result in improved results. The prior art does not teach modification of electrode locations from that specified by the standard 10-20 System when fewer than the full set of electrodes are used.

Various attempts have been made to construct an apparatus for locating EEG electrodes in emergency situations, but none are adequate to meet the needs of an emergency situation for acute brain injury in which rapid and accurate placement of scalp electrodes Is accomplished by individuals who are in attendance to provide emergency and critical care, but who are otherwise non-expert in setting up and recording EEGs. A head template which makes provision for a reduced number of electrodes, and with indicia designed to be read during emergency application, is needed to meet this need.

Systems that rely upon digital EEG technology and which allow EEG data to be transmitted via a computer network to a single expert EEG reader are known. What is needed is a system that presents a turn-key interface to the non-expert personnel who routinely attend acutely brain-injured victims, preventing change or modification of the electroencephalogram parameters by the field technician, while at the same time allowing extensive control over such parameters by a remote expert EEG reader, who is one of a plurality of readers who are part of a network of trained EEG readers.

SUMMARY OF INVENTION

The invention meets this need by providing a simple template and a method which modifies the number of electrode locations from that taught by the standard 10-20 System, specifies a location for the ground electrode, which has indicia that can be quickly and easily read by non-experts during emergency application, and which provides a turn-key interface to the non-expert personnel who routinely attend acutely brain-injured victims, preventing change or modification of the electroencephalogram parameters by the field technician, while at the same time allowing extensive control over parameters by a remote expert EEG reader, who is one of a plurality of readers who are part of a network of trained EEG readers.

A template for the rapid placement of electroencephalogram electrodes on a patient with acute brain injury is provided which comprises a first strap having an outer surface and an inner surface; a second strap having an outer surface, an inner surface, a first end connected to the first strap, and a second end connected to the first strap; a third strap having an outer surface, an inner surface, a first end connected to the first strap at a first junction, a second end connected to the second strap at a second junction, and at least one opening completely through the strap from the outer surface to the inner surface; where the opening in the third strap is positioned approximately 25% of the distance from the first junction toward the second junction. The first strap may further comprise ten openings completely through the first strap from the outer surface to the inner surface, each of the ten openings being approximately equally spaced from the adjacent opening.

An electroencephalogram acquisition unit (AU) for use by an AU operator is provided, each AU comprising a parameter storage for storing a database of electroencephalogram parameter data; an access module coupled to the parameter storage for limiting access by the AU operator to the parameter storage; an electroencephalogram generation module, coupled to the parameter storage for generating an electroencephalogram; and a user interface coupled to the access module and the electroencephalogram generation module for receiving input from the AU operator and for providing output.

Another embodiment of the electroencephalogram acquisition unit further comprises a communications module coupled to the parameter storage providing remote access to the parameter storage.

A system for electroencephalography of a patient with acute brain injury is provided comprising one of the embodiments of the electroencephalogram acquisition unit (AU) described above; a network of electroencephalogram readers; and a communications network for facilitating communication between an AU and the electroencephalogram readers.

A method for electroencephalography of a patient with acute brain injury Is provided comprising the steps of creating a database of electroencephalogram parameter data; storing the database on an electroencephalogram acquisition unit (AU); limiting access to the database by operators of AU; permitting access to the database by remote operator; and generating an electroencephalogram using the database. A further embodiment of the method comprises the steps of selecting a network of electroencephalogram readers, and transmitting the electroencephalogram to one of the plurality of the electroencephalogram readers.

BRIEF DESCRIPTION OF DRAWINGS

These and other features, aspects, and advantages of the present invention will become better understood with reference to the following description, appended claims, and accompanying drawings, where:

FIG. 2 is a pictorial diagram of the right side view of the head template of FIG. 1;

FIG. 3 is a pictorial diagram of the left side view of the head template of FIG. 1;

DETAILED DESCRIPTION

The system, method and apparatus of the present invention can be used for application of electroencephalography in any setting of acute brain injury ("ABI"), including by way of example, the emergency room, Intensive care unit, or field emergencies. For purposes of illustration, the following describes one preferred implementation of the apparatus and the method of using it, and the system of the present invention. As will be apparent to those skilled in the art, the apparatus, method and system described can be easily modified for application in any setting of acute brain injury.

Figures 1, 11:
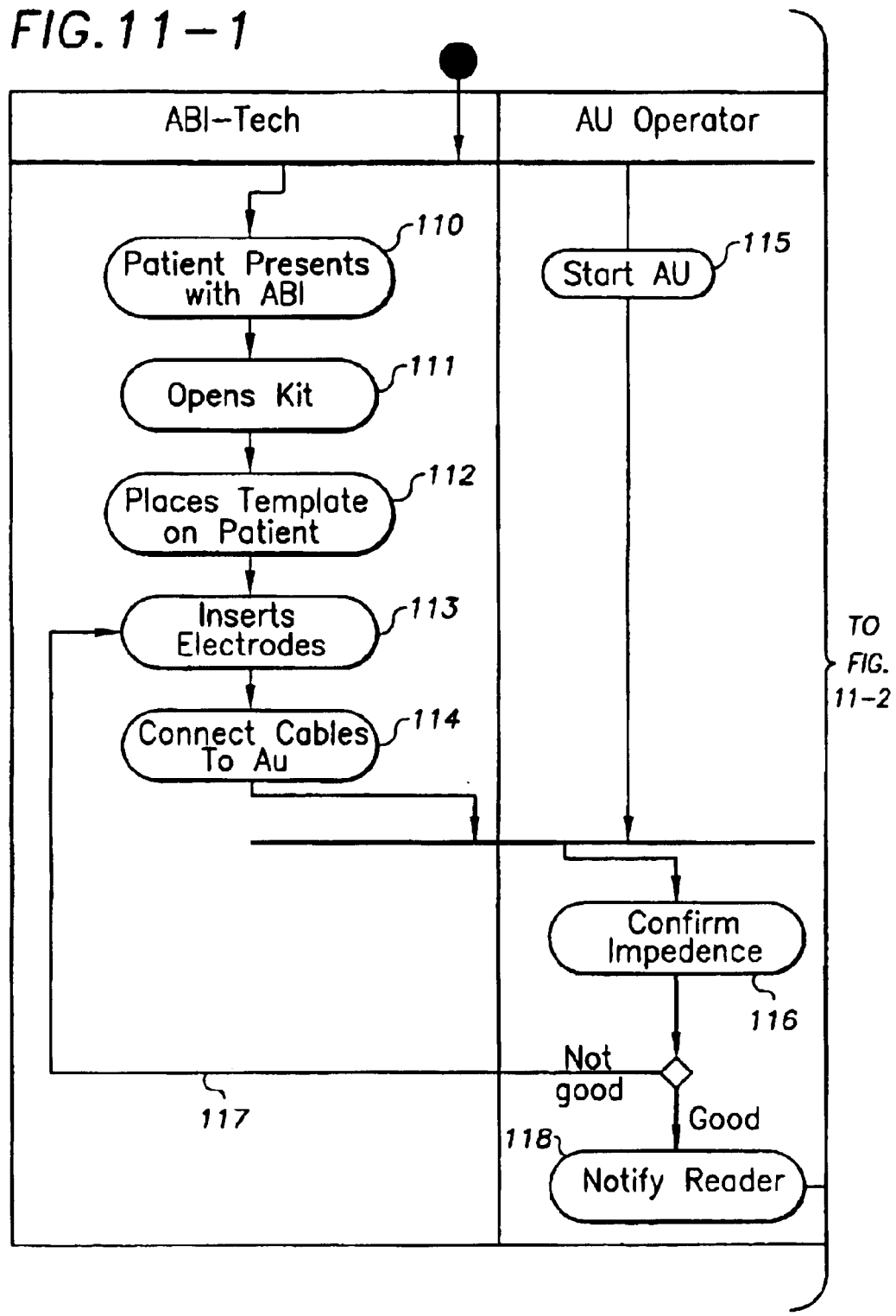
FIG. 11 is a swimlane chart depicting the system according to the present invention.
Figure 12:
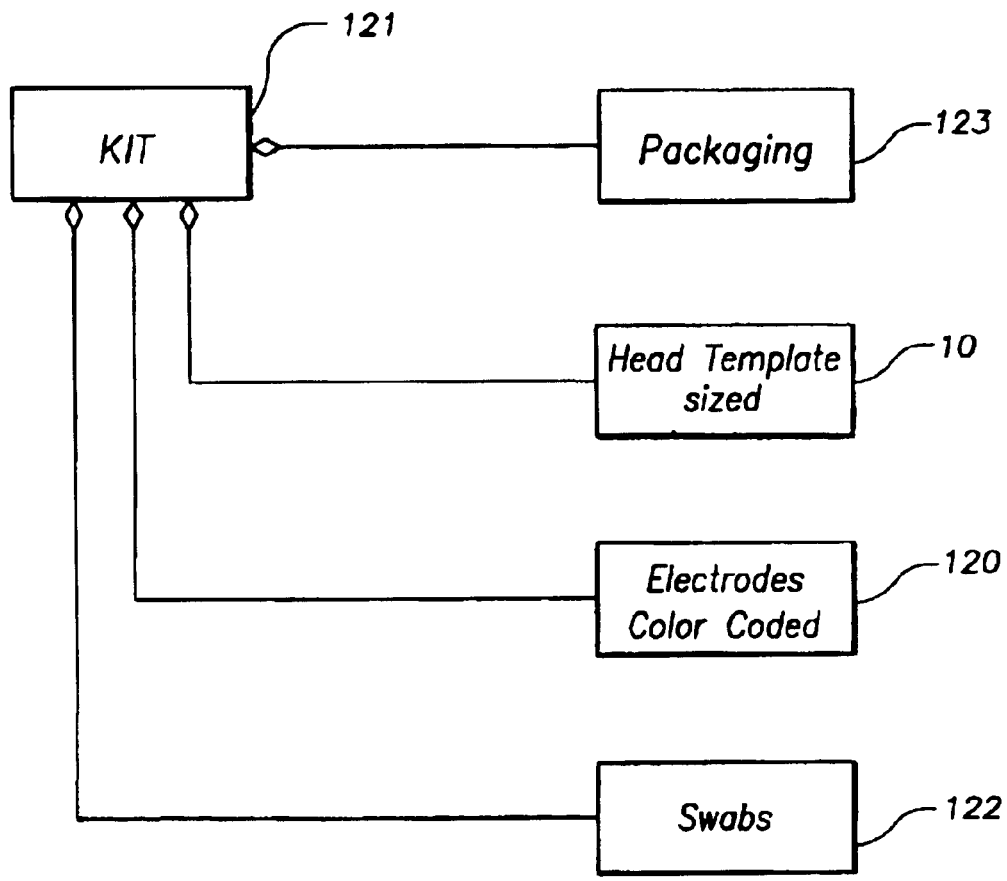
FIG. 12 is a component diagram of a kit according to the present invention.

With reference to FIG. 11, the system initiates with the presentation 110 to emergency personnel of a patient with an acute brain injury ("ABI"). The specific emergency personnel ("ABI-Tech") will depend upon the context; In the emergency room ("ER") it might be a nurse or ER technician, and in a field emergency it might include paramedic personnel. In any of such cases, an ABI-Tech opens 111 a kit 121, as described in FIG. 12. The kit 121 comprises a head apparatus template 10, with reference to FIG. 1, a plurality of individually packaged and sterilized disposable subdermal needle electrodes with attached cables 120, and one or more swabs 121. The packaging 123 for the kit is constructed of a clear plastic with a closeable, resealable top, and with an opaque surface on one side suitable for writing, on which is printed the contents of the kit. The exterior of the packaging for the kit indicates that the kit is to be used on an adult patient, or on a child patient. Other means of packaging for the kit will be evident to those skilled in the art, including boxes or water-proof enclosures, as the environment in which the kit is to be used may require.

Preferably, there are more subdermal needle electrode packages 120 included in the kit than would be required for use in the head apparatus template, in order to anticipate spoilage or failure of the electrode. Thus, in one embodiment the head apparatus template 10 is constructed for positioning of 14 electrodes, and 16 individually packaged and sterilized disposable subdermal needle electrodes with attached cables are included in the kit.

Figure 13:
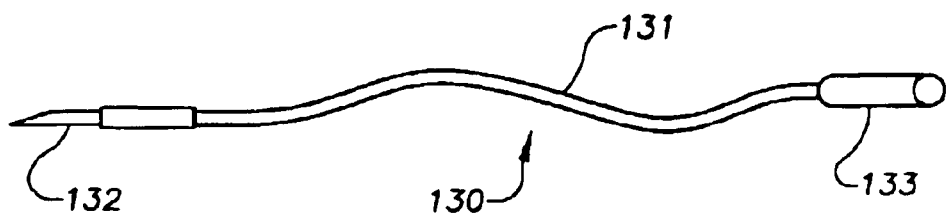
FIG. 13 is a pictorial diagram of a needle electrode and cable assembly.

With reference to FIG. 13, the subdermal needle and cable assembly 130 comprises a needle 132 at a first end corresponding to DIN, 12 mm long, 0.4 mm diameter, attached to a 1 meter cable 131, with a receptor connection 133 at a second end. The length of the cable is not critical to the system. The thickness of the needle is not critical, but a needle of 0.4 mm diameter is preferred. Sterile packages manufactured to these specifications are commercially available. One manufacturer of conforming electrodes is Nicolet-EME GmbH.

In one embodiment of the kit, each cable 131 attached to a subdermal needle electrode 132 and included within the kit is of a different color. In another embodiment, there are 4 red cabled electrodes, 4 yellow cabled electrodes, 2 green cabled electrodes, 2 blue cabled electrodes, and 2 white cabled electrodes, plus 4 more packaged electrodes or varying colors, in the kit 121.

The head apparatus 10 included within the kit 121 may be sized according to the size or age of the patient. Thus, in one embodiment, the kit might contain a head apparatus suitable for an adult, and be so marked on the exterior of the package 123.

The Head Apparatus The ABI-Tech next fits 112 the template onto the patient's head to act as a template for placement of each electrode 132, which the ABI-Tech inserts 113 into the scalp using the openings in the template as a guide.

Figure 4:
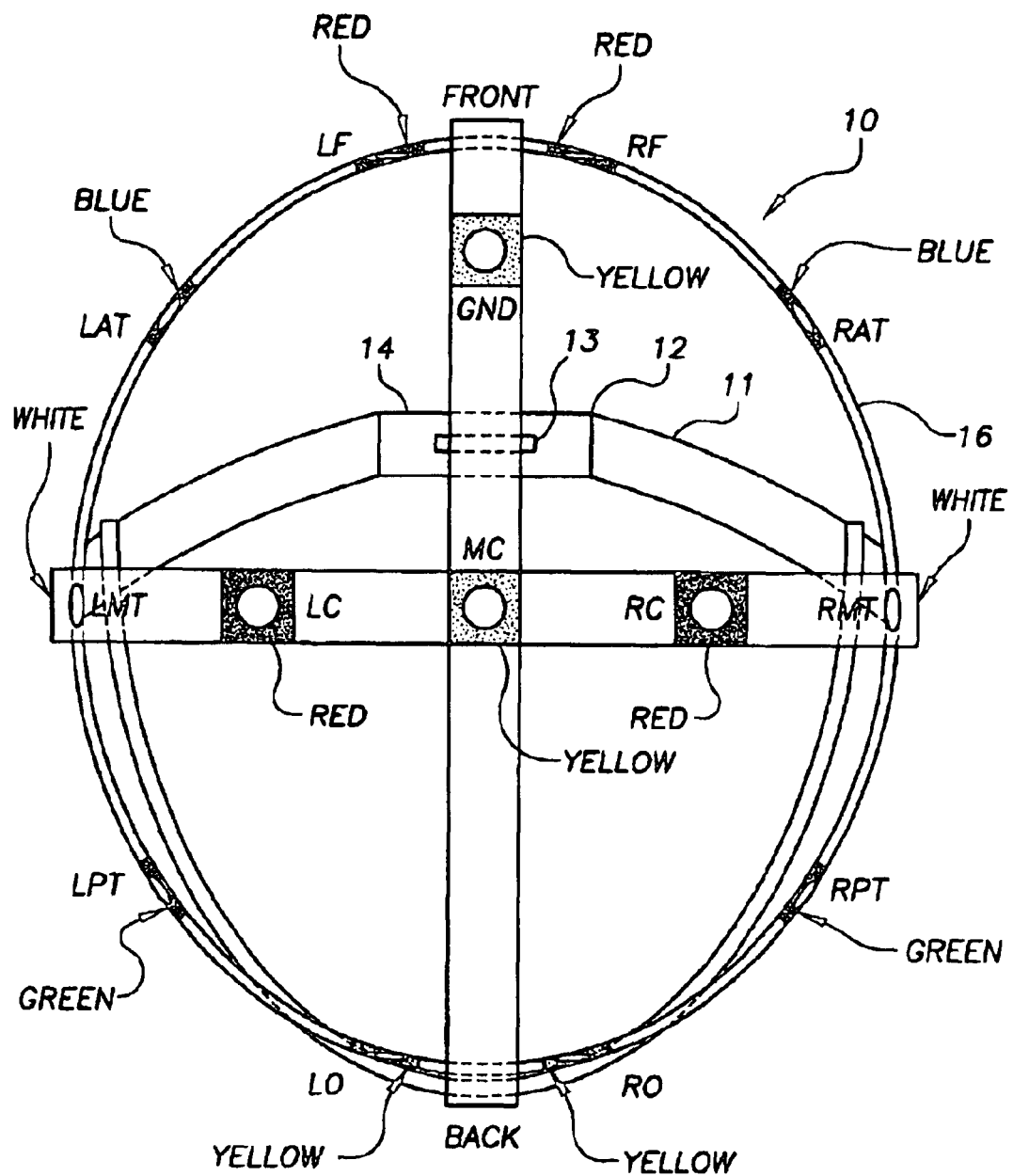
FIG. 4 is a pictorial diagram of a top view of the head template of FIG. 1.

The construction of the head template apparatus 10 is shown in FIG. 2 for a left view, FIG. 3 for a right view, and FIG. 4 for a top view. The template consists of elastic cloth, which can be stretched to fit comfortably over a patient's head, and is then secured with a fastener strap 14 under the patient's chin removeably connected to two jaw straps 11. Preferably, the fastener strap 14 would be easily adjustable and quickly fastened, and so that it would be stable against the patient's chin. This may be accomplished by constructing a fastener at point 12 of VELCRO(r) brand adhesive strips, and by disposing a slit 13 through the length of the chin strap 14, thereby holding the template securely In place against a chin. Bias straps 15 may be added to the template to further secure it in place. A preferred construction for the bias straps 15 connects a left bias strap and a right bias strap to a tab 21 of the template 10 which extends beyond the strap 16 which circumscribes the patient's head, each bias strap removeably connecting to a jaw strap 11.

In one preferred embodiment, the head apparatus 10 is designed specifically for use with sterilized disposable subdermal needle electrodes with attached cables, which are inserted directly under the scalp skin and do not require securing with paste or glue. This embodiment requires no special conduction jellies or chemical contacts, and there is no need for a cushion surface or specialized conduction medium to maintain electrical continuity between the electrode and the patient's head.

The various openings of the straps are color-coded as shown on FIG. 4, and correspond to an identical color on a cable 131 attached to a needle electrode 132, in order to ease rapid placement of the electrodes on the scalp. At each opening in the strap, a needle electrode may be inserted through the hole into the scalp.

In one preferred embodiment, disposable subdermal needle electrodes are used. The apparatus can be designed, however, to accommodate a variety of electrodes as be determined by the clinical purpose, as will be apparent to those skilled in the art. The electrode can be held in place by the elastic cloth adjacent to the hole if this proves necessary.

Figure 5:
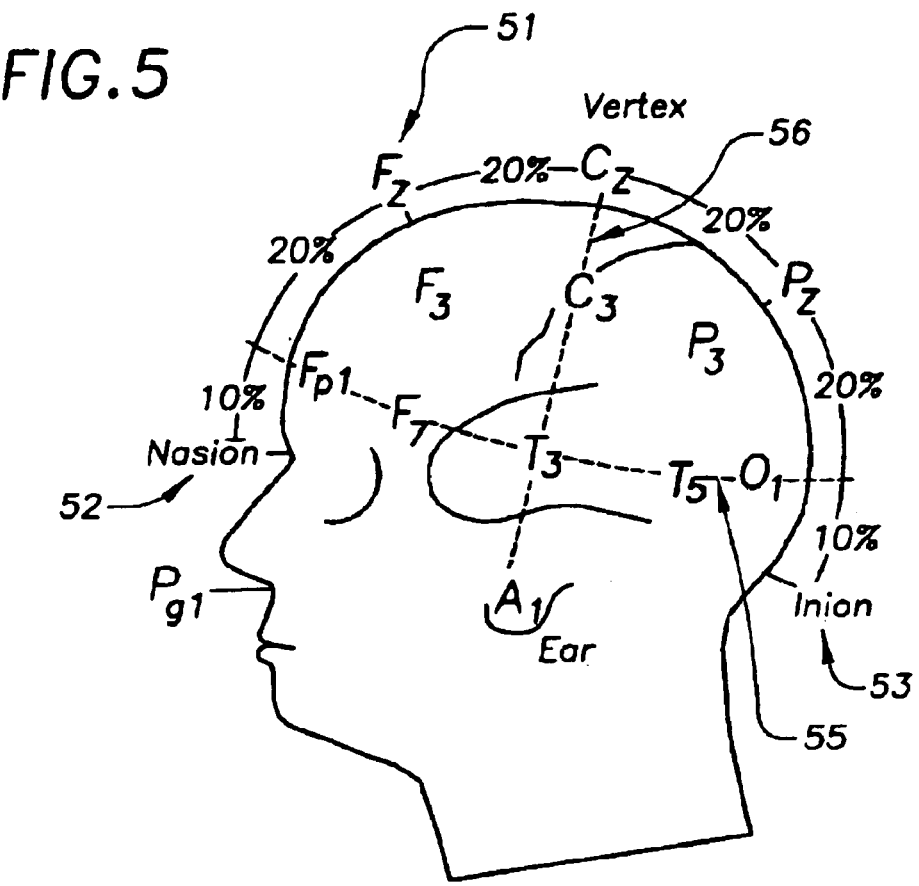
FIG. 5 is a pictorial diagram of the left side view of the positions of electrodes according to the International 10-20 System.
Figure 6:
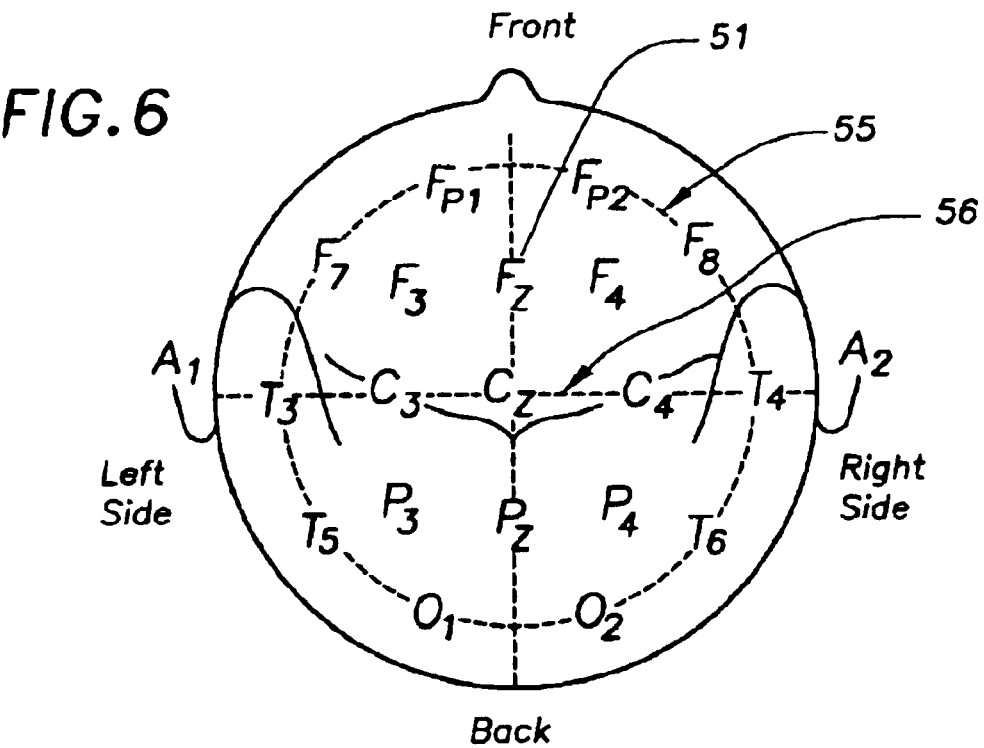
FIG. 6 is a pictorial diagram of the top view of the positions of electrodes according to the International 10-20 System.

The openings of the template deviate in an important aspect from the standard 10-20 electrode placement locations for EEG electrode placement. The standard 10-20 System teaches a system of measurement from the nasion and inion positions for placement of scalp electrodes that requires 21 electrodes, as shown in FIG. 5 and FIG. 6, and which are commonly labeled Fp1, Fp2, F7, F3, Fz, F4, F8, A1, T3, Cz, C3, C4. T4, A2, TS, P3, Pz, P4, T6, O1, and O2. It is known that the electrode locations A1 and A2 are hard to secure, and frequently generate artifacts, and so may be eliminated when not doing referential recordings.

The Fz electrode acts as a ground, analogous to an antenna. As shown in FIG. 5, in the standard 10-20 Systerm the Fz location 51 lies on a centerline between the nasion 52 and inion 53, and approximately mid-way between a line 55 which circumscribes the patient's head, and the line 56 which transverses the patient's head.

When fewer than 21 electrodes (19 if the A1 and A2 locations are not used) are used, the distances between electrodes correspondingly increases. This has been found to generate greater noise in the EEG recordings. Extrapolation from knowledge of the electrophysiology of the inter-electrode distances and experimentation has demonstrated that by moving the location of the Fz from that specified in the 10-20 System, a less noisy EEG recording will result. What is desired is to establish the Fz electrode over a neutral portion of the patient's skull, where it still registers cerebral activity but does not favor one activity over another.

Figure 7:
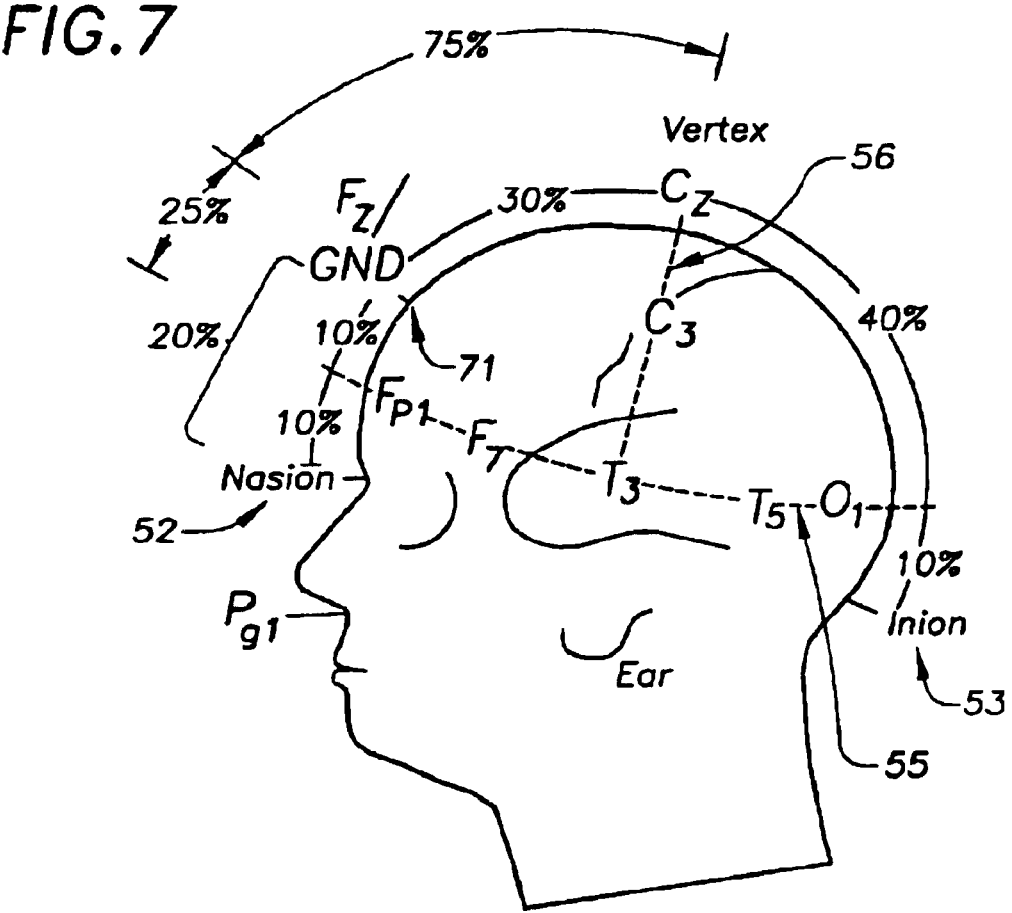
FIG. 7 is a pictorial diagram of the left side view of the positions of electrodes according to the present invention.
Figure 8:
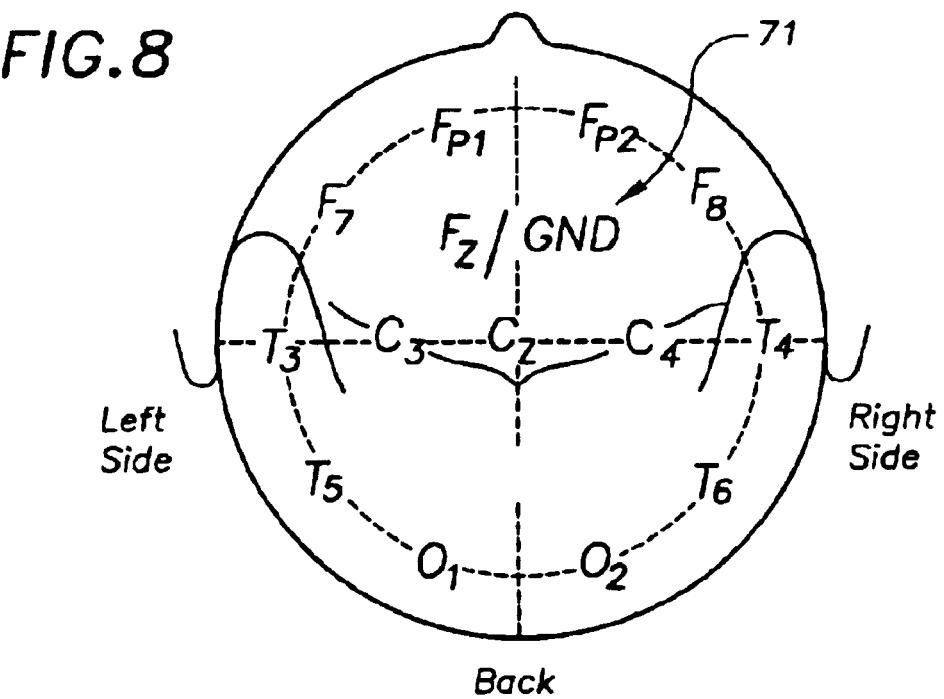
FIG. 8 is a pictorial diagram of the top view of the positions of electrodes according to the present invention.

Study has demonstrated that locating the Fz electrode at a position approximately 25% of the distance from the line 55 which circumscribes the patient's head toward the line 56 which transverses the patient's head provides a better ground reference when using fewer than 21 (or 19 if the A1 and A2 locations are not used) electrodes. As shown in FIG. 7 and FIG. 8, the Fz location 71, now marked as "Gnd" on FIG. 7 and FIG. 8, lies 25% of the distance from the line 55 which circumscribes the patient's head toward the line 56 which transverses the patient's head. If measured with reference to the standard skull points of the nasion 52 and inion 53, this location for the Fz electrode would be approximately 20% of the distance from the nasion to the inion, as shown in FIG. 7. This position of the Fz electrode may be varied by approximately half a centimeter in any direction and still achieve the desired result. This intentional variation from the 10-20 System does not interfere with topographic interpretation of EEG waveforms from specific cerebral sites.

A template having this new configuration for the Fz electrode location will comprise a first strap having an outer surface and an inner surface; a second strap having an outer surface, an inner surface, a first end connected to the first strap, and a second end connected to the first strap; a third strap having an outer surface, an inner surface, a first end connected to the first strap at a first junction, a second end connected to the second strap at a second junction, and at least one opening completely through the strap from the outer surface to the inner surface; where the opening in the third strap is positioned approximately 25% of the distance from the first junction toward the second junction.

In one preferred embodiment of the template 10, there is no strap containing openings for F3/F4 pair of electrodes or P3/P4 pair of electrodes, the opening for the Pz electrode is eliminated, and the Fz electrode is located in the new position as explained above, resulting in satisfactory EEG readings. In that event, the template will have an opening geometry consisting essentially of thirteen openings located according to the International 10-20 System specification for positioning scalp electrodes at points Fp1, Fp2, F7, F8, T3, T4, Cz, C3, C4, TS, T6, O1, and O2, and a fourteenth opening for the Fz electrode 71 located approximately 20% of the distance from the nasion 52 to the inion 53, as shown in FIG. 7. The Fz location on FIG. 7 is alternatively marked as "Gnd." To assist in placement of the template on a patient's head, tabs indicating the location of the nasion 52 and inion 53 may be added to the template. In a template having this opening geometry the first strap will comprise ten openings completely through the first strap from the outer surface to the inner surface, each of the ten openings being approximately equally spaced from the adjacent opening. Further, the second strap will comprise a first opening, a second opening and a third opening, each of the openings being completely through the strap from the outer surface to the inner surface, the second opening of the second strap will be approximately equidistant between the first end of the second strap and the second end of the second strap, and the first opening of the second strap and the third opening of the second strap will be approximately equidistant from the second opening of the second strap.

Figure 10:
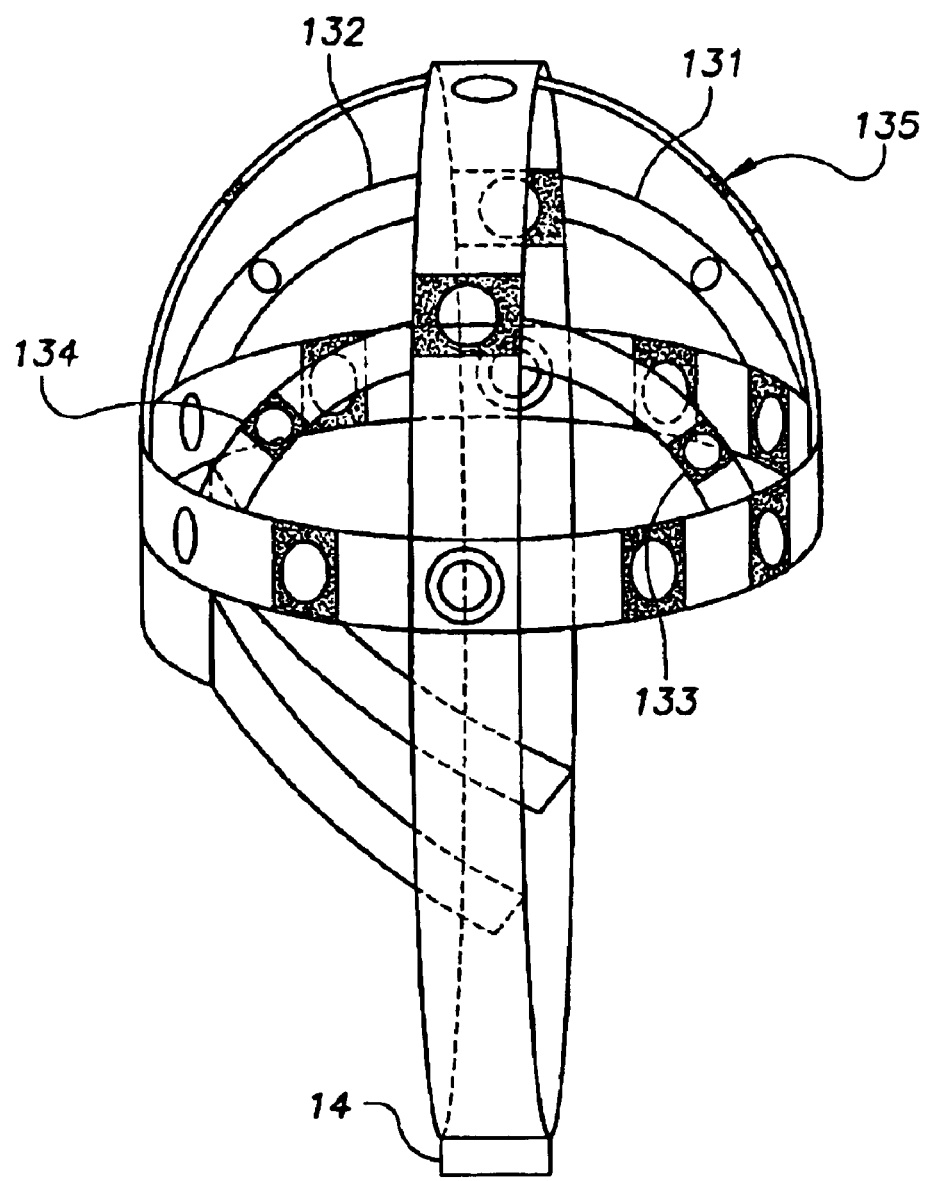
FIG. 10 is a pictorial diagram of the right side view of a further embodiment of the head template of FIG. 1.

It may be preferable to have a template which can be used for both emergency and non-emergency situations, as shown in FIG. 10. In that embodiment there will be further straps 131, 132, 133, and 134 which contain openings, and an additional opening 135 corresponding to the standard 10-20 placement for Fz electrodes. In emergency situations these locations can be unused. In a further embodiment straps on the template which have openings corresponding to these unused locations can be cut off, or the locations can be ignored. It would be preferred to have indicia adjacent to the openings that may be disregarded in an emergency. Alternatively, these locations can be left unmarked as shown in FIG. 10, in distinction to the colorcoding for the emergency openings.

In another embodiment, the first strap can have two ends. These ends can be connected to each other so that the first strap forms a closed loop. Preferably, the first end of the first strap comprises a connector, and the second end of the first strap comprises a connector, where the connector on the first end of the first strap is configured to mate with the connector on the second end of the first strap. A snap connector is one such connector. Alternatively, the ends can each be connected to another means, such as a ring.

It would be possible to eliminate further electrode positions according to the present invention, but with decreasing reliability, if homologous pairings are maintained. Variation In spacing of the individual openings in the template should be kept within a tolerance of approximately 0.5 cm in any direction. If further deviation is made in the spacing of openings on the first strap of the template, each of the remaining openings should be approximately equally spaced from the adjacent opening.

Figure 9:
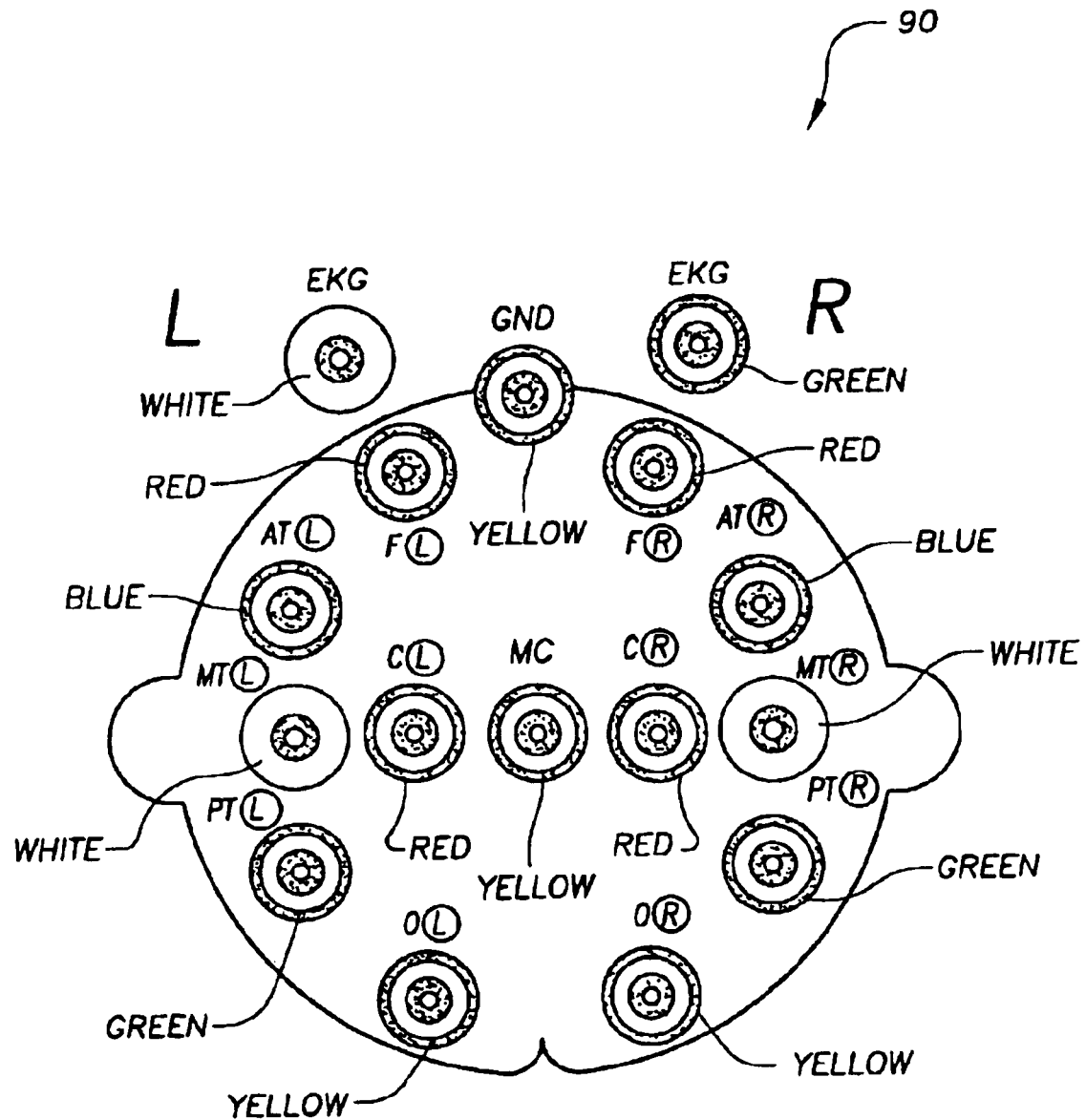
FIG. 9 is a pictorial diagram of the indicia on the junction box according to the present invention.

The head template can be positioned in any head or body position including supine, sitting, or erect. In each case, however, it is preferred that the electrodes be inserted while the ABI-Tech is facing the vertex of the patient's head. In a preferred embodiment, the template 10 is provided with indicia proximate to the openings in the straps which appear to be inverted, as shown in FIG. 2 and FIG. 3, but which will appear correctly oriented when viewed by an ABI-Tech looking at the template while facing the vertex of the patient's head. The indicia comprise legends MC, RC, LC, LO, RO, LPT, RPT, LMT, RMT, LAT, RAT, LF, RF and Gnd as shown in FIG. 2 and FIG. 3. In a further embodiment, the indication for "left" and "right" in the indicia comprise the letter "L" or "R" within a circle. As shown in FIG. 9 as displayed on the junction box, the indicia then read MC, CcircleL, CcircleR, OcircleL, OcircleR, PTcircleL, PFcircleR, MTcircleL, MTcircleR, ATcircleL, ATcircleR, FcircleL, FcircleR and GND.

The legend associated with the standard 10-20 System makes reference to the underlying cerebral lobe. Thus, by way of example, O1 lies proximate to the occipital lobe, T3 lies proximate to the temporal lobe, Fp1 lies proximate to the frontal lobe, and so on. The difficulty in the standard legend, however, is that it gives no indication to a non-expert in an emergency situation which hemisphere of the head is described.

Thus, a non-expert will not appreciate that O1 lies on the left hemisphere of the head as viewed from the vertex, and O2 lies on the right. Therefore, the legend on the template 10 as shown in FIG. 2 and FIG. 3 intentionally differs from standard terminology and is easily interpreted by the ABI-Tech using an "L" prefix for the left positions, "R" for right positions, and "Gnd" for the ground position Fz on third strap and attached to outer surface of the third strap. As shown in FIG. 9, this legend is carried through to openings on a label 90, which is attached to a junction box 151, with reference to FIG. 15. The receptor end 133 of each needle assembly 130 mates to a connector in the junction box. The legend results in unambiguous terminology for the non-expert and reliable matching of the cables to the correct position on the junction box 151.

Using the combination of color-coding and legend as a guide, the ABI-Tech connects 114 the receptor end 133 of each needle assembly 130 to the acquisition unit, according to the present invention.

Figure 1:
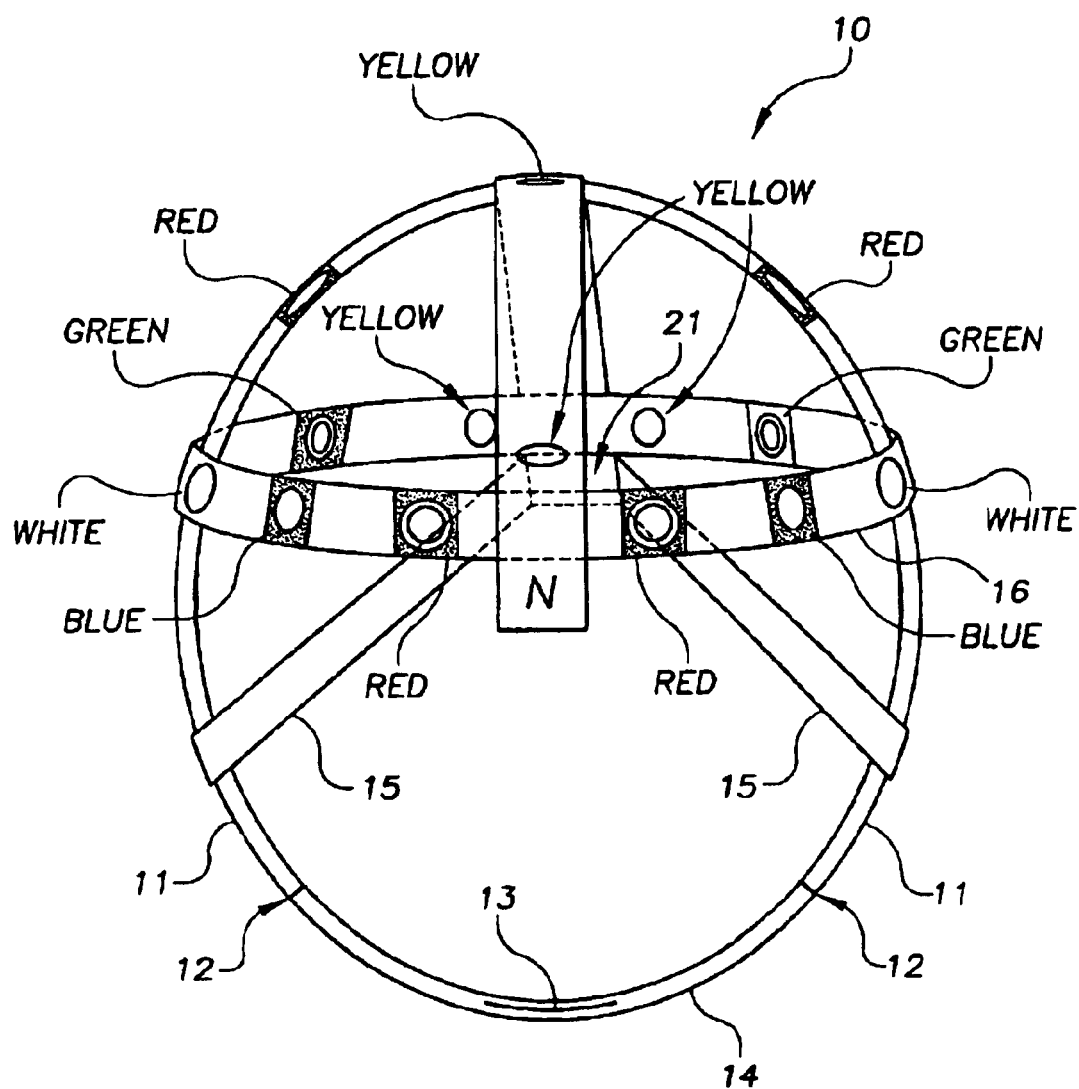
FIG. 1 is a pictorial diagram of a front view of a head template apparatus according to the present invention.

The use of color coding indicia on the template, alone or in addition to the inverted legend, further eliminates ambiguity for the non-expert. As shown in FIG. 1, the outer surface of the strap adjacent to electrode positions Cnd, MC, LO and RO are colored yellow, LC, RC, LF and RF are colored red, LAT and RAT are colored blue, LPT and RPT are colored green, and LMT and RMT are colored white. As shown in FIG. 9, the corresponding receptor point on the junction box has a corresponding color adjacent to the opening.

Acquisition Unit

Figure 15:
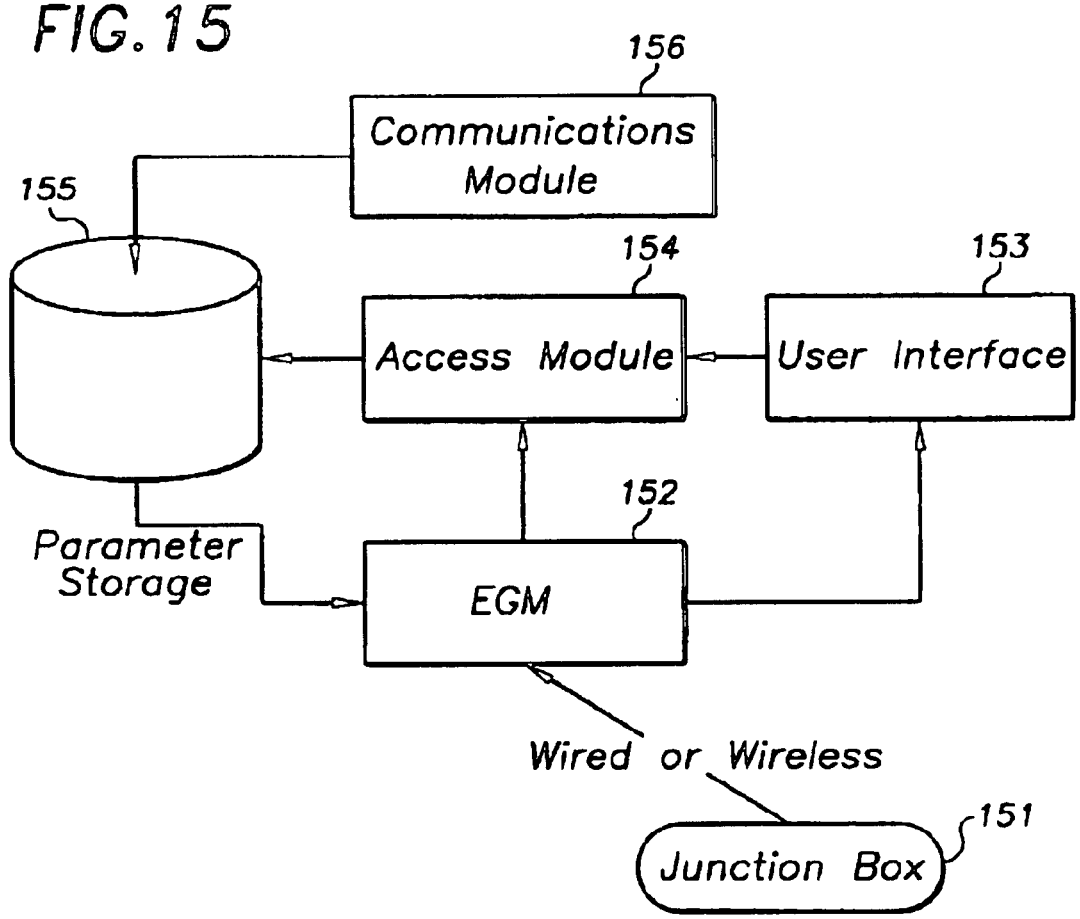
FIG. 15 is a component diagram showing the modules of the acquisition unit according to the present invention.

With reference to FIG. 15, a junction box 151 is connected by an appropriate means to an acquisition unit (AU), which comprises electroencephalogram generation module 152, a user interface 153, an access module 154, parameter storage 155, and a communication module 156.

A suitable electroencephalogram generation module (EGM) comprises a central processing unit (CPU), which has been programmed to run digital EEG software in accord with the present invention. The manner of connection can vary, and in one preferred embodiment the connection is made by a direct connect cable from the junction box to an input port on the EGM. Various other ways to connect the junction box to the EGM will be evident to those skilled in the art, including both wired and wireless. By adding a wireless transmitter to the junction box 151 and a receiver to the EGM, a wireless connection could be accomplished, permitting the AU to be placed at some physical distance from the patient. This would enable, for example, paramedics to place the head template and electrodes on a patient disposed in an accident location, while the AU was located in nearby emergency vehicles.

The requirements for the CPU within the EGM can vary as the surrounding physical environment dictates. For example, a CPU located in an ER or an ICU would not have to be contained in a portable unit, while a CPU used in field situations should be contained in an enclosure that was durable, sturdy, portable, and stable. A standard Pentium-type personal computer with hard drive and input ports would be able to operate the needed software, which is part of the EGM.

In an ER or ICU environment it is preferred to mount the AU on a cart which can be readily moved. The EGM is coupled to a user interface 153, comprising a monitor, which is used to display the resulting EEG and to communicate information to the AU operator, and a keyboard to receive information from the AU operator. In one embodiment, the monitor is a flat screen integrated into the case which contains the EGM. Other variations will be readily apparent to those skilled in the art. For desktop AU units place on a cart, a standard SVGA monitor will be an acceptable alternative. Preferably, the monitor will be capable of displaying color information. The user interface may alternatively utilize a touch screen.

In one preferred embodiment, the EGM has electronic components which can tolerate being in the "on" mode almost continuously, in order to avoid time delays for "booting up" the system. With reference to FIG. 11, the AU operator either starts 115 the EGM module within the AU, or confirms that it is on. Immediately upon connection of the cables to the AU 114, the EGM begins processing of the received electrical signals, and display of the EEG of the connected patient appears on the user interface 153.

It is contemplated that the operator of the AU is either the ABI-Tech who placed the template on the patient and inserted the needle electrodes, or another non-expert person such as an ER technician, nurse, paramedic, ICU nurse, nurses' aide, or other person who is personally attending patients with ABI at or near the sites of their injuries. The AU operator is assumed to be non-expert in the technical details of the EEG, and it is important that the EEG be displayed according to predetermined default parameters including time base, amplitude, sensitivity, low frequency filter, high frequency filter settings, and 60 Hz notch filter settings. A database of these default parameters are created, and are stored in parameter storage 155, which is part of the AU. In a preferred embodiment, these settings are neither changeable nor controllable by the on-site AU operator, except by password access. This limited access is accomplished by an access module 154. Several ways of establishing password access between a user interface and storage will be evident to those skilled in the art.

Proper matching of electrode impedance is important for a good EEG reading. The software which is part of the EGM 152 assists the AU operator in confirming impedance 116. After the EEG appears on the user interface, a window automatically opens showing a scalp map representing the positions of the EEG needle electrodes on the patient's head. If a color monitor has been included in the user interface 153, each needle position will appear with an adjacent color indicia either green or red; thereby indicating acceptable (green) impedance range or unacceptable (red) impedance range. This display cues the operator about problems with one or more specific electrodes and their positions, which may require manipulation or reinsertion of the needle by the ABI-Tech 117 to improve the quality of the recording. It will be apparent to those skilled in the art that alternate codings for acceptable/unacceptable impedance ranges could be used, particularly if a monochromatic monitor were used.

Figure 14:
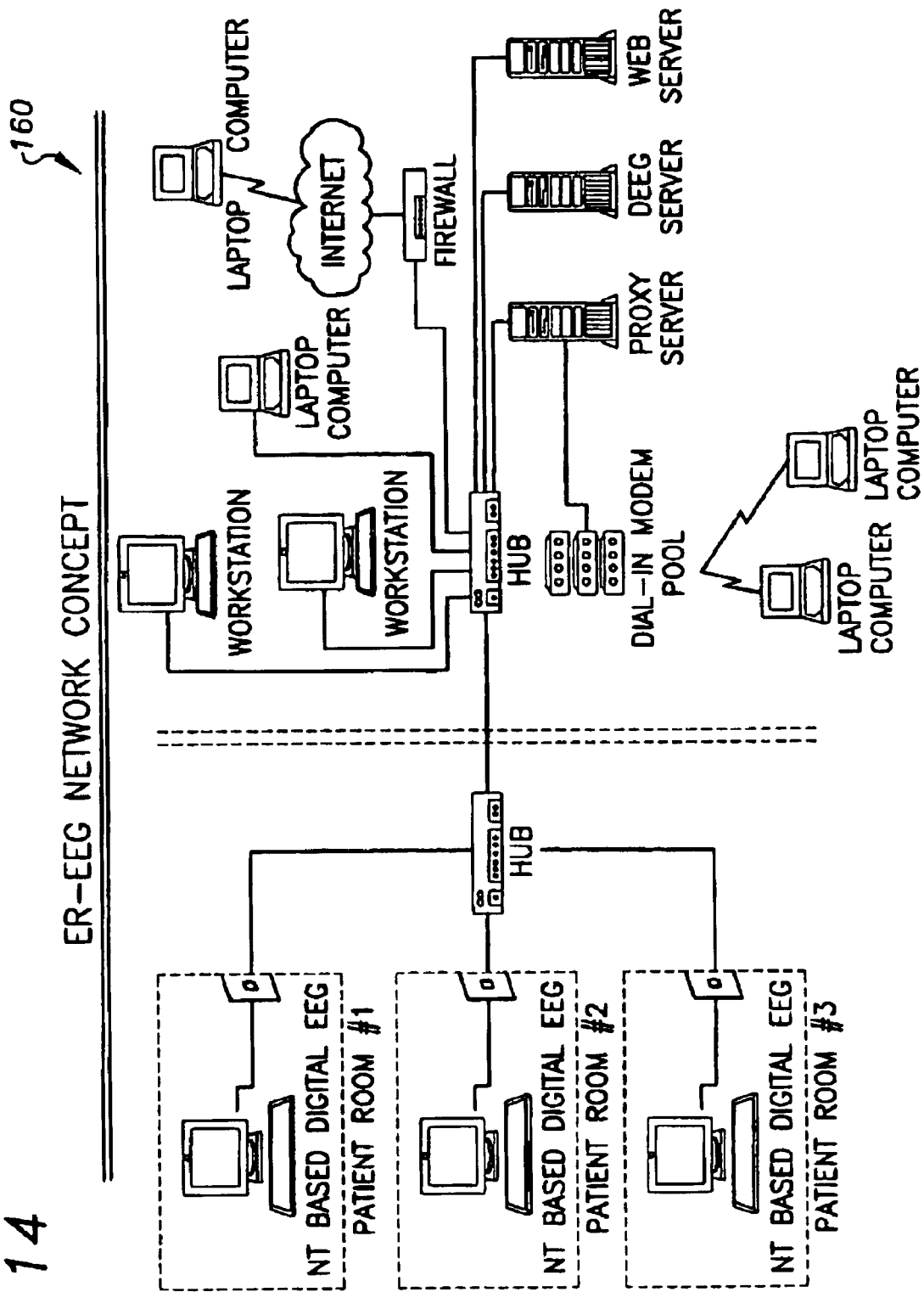
FIG. 14 is a network diagram of a communications network according to the present invention.

The communications link to the Remote EEG Reader Network is shown in FIG. 14. The detail of the Remote EEG Reader Network is described below.

Figure 16:
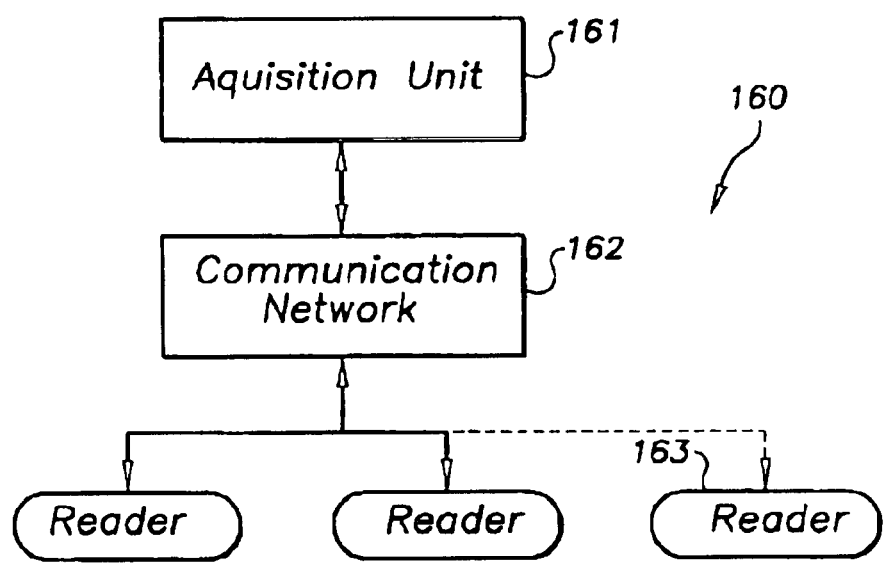
FIG. 16 is a network diagram of the system according to the present invention.

The use of automatic cueing windows in the EGM software to instruct the operator in basic terms through each sequential step continues with a quadrant window which automatically opens to cue the operator to notify or page a designated remote EEG reader 163, with reference to FIG. 16, that an EEG is being acquired and will be transmitted through the network 162. The Remote EEG Reader 163 selected to receive the transmission is determined by 1) pop-up, programmed cue on AU, 2) programmed pull-down menu on AU, 3) printed hardcopy of EEG Reader schedule available to AU operator, 4) programmed schedule on central server, or 5) other method of determining scheduled on-call personnel known to those familiar with the art. The AU operator is given the option to include a brief text message with the notification. After an appropriate time, preferably one to two minutes, if the operator has not sent the notification, the AU automatically sends it via pager, mobile phone or other communication means. This prevents the interruption of the transmission should something interfere with the AU operator.

In another embodiment, a central server notifies or pages a designated remote EEG reader that an EEG is being acquired and will be transmitted.

In one preferred embodiment, with reference to FIG. 14, a sending AU communicates with a single central server hub, which may then re-distribute the signal to one or more other servers, who in turn can distribute the signal to any individual remote reader 163.

Upon receiving notification that an EEG is being acquired and will be transmitted, the Remote EEG Reader connects to the network. When he or she successfully connects to the network, thereby becoming a remote node, a window on the AU user interface displays a message that the "EEG reader is online." An accompanying light signal stays on the AU for the duration of the time that the EEG reader is connected to the network. In another embodiment, a color change is made to the border of the window to indicate that the EEC reader is connected to the network. Other visual indicia to indicate that the EEG reader is online are possible, and will be evident to those skilled in the art.

The next window on the AU cues the AU operator to enter the required patient demographic data, including billing information if known. In one embodiment, the system is able to scan bar-coded patient data to minimize operator data entry error.

The next window on the AU user interface cues the operator to enter the necessary clinical information about the patient's condition, medications, and other relevant medical information required for clinical correlation of the EEG data. Input of information can be provided in the form of pull-down menus, from which the operator selects the appropriate choices with a simple keystroke or mouse click.

In one embodiment, telephonic voice communication is incorporated in the AU to allow convenient verbal communication in a hands free fashion between the AU operator and the EEG reader. This is achieved with a separate, dedicated phone line and speakerphone for each AU, or with an "in-band" connection using telephonic remote control software.

The central server assigns a sequential number to the AU for identifying the study, the date, time, duration, and location of the study, as well as the name and identifying number of the expert reader. The centralized record management allows consistent patient records to be generated, archived, and referenced.

Before the study is terminated, a window appears at the AU cuing the operator to confirm that all of the required information and data have been entered. The study is then archived in real-time by the central server and made accessible to local and remote nodes quickly.

In one embodiment, the AU also contains a data base program, so that any or all of the study or related data such as demographic, clinical, or financial information can be reviewed and analyzed by selected field inspection.

The Remote EEG Reader Network

A Remote EEG Reader Network is comprised of a plurality of expert EEG readers 163 who are selected according to systematic training, demonstrated proficiency, established credentials, reputation, and recommendations as to their level of competence in interpreting digital EEC studies. The expert EEG readers' orientation includes a systematic training program, wherein the readers are instructed in the use of the EEG network hardware and programmatic components, standardized vocabulary for interpreting and reporting EEG results are taught, and uniform standards of performance are established. Each expert EEG reader is given written guidelines and reference material to ensure consistency of interpretations and correlations.

At any given time, one or more EEG Readers who have been selected to be part of the network 160 will be on-call, ready to receive a communication from a sending AU 161. The network can operate as a one-to one, one-to many, or many-to-many relationship between sending AU units and EEG Readers. In one preferred embodiment, each EEG Reader will provide service to several AU units while on call assigned on a geographical basis, clinical basis, or on a rotating basis.

The use of multiple readers decreases the potential for delay in AU reading, which otherwise might be queued waiting for a single reader to become available.

Communication between the AU and EEG Reader can be by direct dial-up through phone lines, local area networks, wide area networks, or through the global world wide web using an appropriate communication protocol. The communication link 162 can also use alternative and emerging forms of digital communication using wireless technology. These include existing and future generations of digital mobile telephones and palm-sized organizers such as the Palm V(r) and Palm VII(r). In addition, web TV displays and satellite-mediated connections are additional alternatives.

Regardless of the mode of communication linkage, the EEC reader is presented with the same data interface. This universal interface allows for consistency in displaying the EEG and reporting results.

The EEG reader accesses the central server through one of several communication connections, such as a digital local area network, a digital wide area network that includes: straight telephone modem access, or in one preferred method, through an Internet connection using wired or wireless technology. Using the Internet, the EEG reader accesses a web page, which guides the EEG reader via buttons, icons, and/or hyperlinks, to the EEG study intended for his interpretation.

Privacy and security of access are protected by a combination of methods including passwords, firewalls, encryption technology, and dial-back confirmation.

Once accessed by the EEG reader, the EEG data are displayed 1191 on the reader's computer monitor for his interpretation.

Through the server connection to the communications module 156 in the AU, in distinction to the limited control afforded the AU operator, the EEG reader 163 has remote access and control 1192 over the parameter storage 155, including the EEG amplifier and display variables, low frequency filter, high frequency filter, amplitude, sensitivity, 60 Hz notch filter, time base, and montage selection. The EEG reader 163 can adjust these display variables remotely in order to produce the combination and format most suitable for interpretation of the record given the clinical context. The EEG reader can also adjust these variables on his screen independent of the default display on the AU monitor visible to the operator at the transmission site.

In another embodiment, video telemetry imaging from the operator site to the EEG reader is incorporated for the EEG reader to confirm or modify the technical set up at the transmitting site.

The EEG reader has the option of displaying the raw digital EEG as quantitative EEG frequency analysis data. This is accomplished by the EEG reader activating an application program to perform quantitative EEG frequency analysis on the raw digital EEG data.

Using this option, the EEG reader can see the EEG data displayed as compressed spectral array, in graphical or topographic displays of absolute and relative alpha, theta, delta, and total power bands, or in other quantitative formats.

The EEG reader communicates his interpretation 1193 of the EEC to the AU operator or other designated individual at the transmitting site. For example, if the acquisition unit transmits an EEG from an ER, the EEG reader communicates the interpretation to the emergency department physician.

Communication of the EEG interpretation to the transmitting site 1194 is accomplished by several methods, including computer faxing, e-mail, or voice communication over the telephonically equipped AU.

The expert EEG reader has the option of selecting the interpretation from a pull down menu in which major clinical correlations are described for different classes of interpretation.

Once selected from the menu and confirmed by the EEG reader, the interpretation is automatically transmitted 1194 back to the AU, is displayed in a window, stored and automatically printed out.

The remote expert EEG reader will remain available to the acquisition unit operator or physician at the transmitting site for additional communication, such as a "mini-consultation" if desired.

Random audits are part of the quality control procedures to ensure competent and high quality interpretation by the expert EEG readers. Performance profiles of expert EEG readers are maintained through the network database as a quality control measure.

Failsafe and redundant communication systems will ensure that every ER-EEG is promptly read and reported.

Although the present invention has been discussed in considerable detail with reference to certain preferred embodiments, other embodiments are possible. Therefore, the scope of the appended claims should not be limited to the description of preferred embodiments contained in this disclosure.

I claim:

1. An electroencephalogram acquisition unit (AU) for use by an AU operator, each AU comprising:
   a parameter storage for storing a database of electroencephalogram parameter data, wherein the parameter data comprise amplifier and display variables;
   a communications module coupled to the parameter storage for remote access to and control of the parameter storage by a remote electroencephalogram reader; and
   an access module coupled to the parameter storage for limiting access by the AU operator to the parameter storage.

2. The acquisition unit (AU) of claim 1, further comprising:
   an electroencephalogram generation module, coupled to the parameter storage for generating an electroencephalogram; and
   a user interface coupled to the access module and the electroencephalogram generation module, the user interface for receiving input from the AU operator and for providing output.

3. The acquisition unit (AU) of claim 1, wherein the amplifier and display variables comprise parameter data selected from the group consisting of low frequency filter settings, high frequency filter settings, notch filter settings, amplitude, sensitivity, time base, and montage selection.

4. A system for electroencephalography of a patient with acute brain injury comprising:

an electroencephalogram acquisition unit (AU) for use by an AU operator, wherein the AU comprises a parameter storage for storing a database of electroencephalogram parameter data, the parameter data comprising amplifier and display variables;

a network of electroencephalogram readers; and a communications network for facilitating communication between the AU and the electroencephalogram readers, wherein electroencephalogram parameters of the AU are controllable by the electroencephalogram readers.

5. The system of claim 4, where the electroencephalogram acquisition unit comprises:

an access module coupled to the parameter storage for limiting access by the AU operator to the parameter storage; and a communications module coupled to the parameter storage for remote access to the parameter storage.

6. The system of claim 5, further comprising a template for the rapid placement of electroencephalogram electrodes on a patient with acute brain injury comprising a first strap having an outer surface and an inner surface; a second strap having an outer surface, an inner surface, a first end connected to the first strap, and a second end connected to the first strap; a third strap having an outer surface, an inner surface, a first end connected to the first strap at a first junction, a second end connected to the second strap at a second junction, and at least one opening completely through the strap from the outer surface to the inner surface; and where the opening in the third strap is positioned approximately 25% of the distance from the first junction toward the second junction.

7. The system of claim 5, where the electroencephalogram acquisition unit further comprises:

an electroencephalogram generation module, coupled to the parameter storage for generating an electroencephalogram; and a user interface coupled to the access module and the electroencephalogram generation module, the user interface for receiving input from the AU operator and for providing output.

8. The system of claim 7, further comprising a template for the rapid placement of electroencephalogram electrodes on a patient with acute brain injury comprising a first strap having an outer surface and an inner surface; a second strap having an outer surface, an inner surface, a first end connected to the first strap, and a second end connected to the first strap; a third strap having an outer surface, an inner surface, a first end connected to the first strap at a first junction, a second end connected to the second strap at a second junction, and at least one opening completely through the strap from the outer surface to the inner surface; and where the opening in the third strap is positioned approximately 25% of the distance from the first junction toward the second junction.

9. The system of claim 4, further comprising a template for the rapid placement of electroencephalogram electrodes on a patient with acute brain injury comprising a first strap having an outer surface and an inner surface; a second strap having an outer surface, an inner surface, a first end connected to the first strap, and a second end connected to the first strap; a third strap having an outer surface, an inner surface, a first end connected to the first strap at a first junction, a second end connected to the second strap at a second junction, and at least one opening completely through the strap from the outer surface to the inner surface; and where the opening in the third strap is positioned approximately 25% of the distance from the first junction toward the second junction.

10. The system of claim 4, wherein the amplifier and display variables comprise parameter data selected from the group consisting of low frequency filter settings, high frequency filter settings, notch filter settings, amplitude, sensitivity, time base, and montage selection.

11. A method for electroencephalography of a patient with acute brain injury comprising the steps of:

creating a database of electroencephalogram parameter data, wherein the parameter data comprise amplifier and display variables;

storing the database on an electroencephalogram acquisition unit (AU);

limiting access to the database by operators of the AU;

permitting access to and control of the database by a remote operator; and generating an electroencephalogram using the database.

12. The method of claim 11, further comprising the steps of:

selecting a network of electroencephalogram readers; and transmitting the electroencephalogram to one of the plurality of electroencephalogram readers.

13. The method of claim 12, further comprising the step of providing a template for the rapid placement of electroencephalogram electrodes on a patient with acute brain injury comprising a first strap having an outer surface and an inner surface; a second strap having an outer surface, an inner surface, a first end connected to the first strap, and a second end connected to the first strap; a third strap having an outer surface, an inner surface, a first end connected to the first strap at a first junction, a second end connected to the second strap at a second junction, and at least one opening completely through the strap from the outer surface to the inner surface; and where the opening in the third strap is positioned approximately 25% of the distance from the first junction toward the second junction.

14. The method of claim 11, further comprising the step of providing a template for the rapid placement of electroencephalogram electrodes on a patient with acute brain injury comprising a first strap having an outer surface and an inner surface; a second strap having an outer surface, an inner surface, a first end connected to the first strap, and a second end connected to the first strap; a third strap having an outer surface, an inner surface, a first end connected to the first strap at a first junction, a second end connected to the second strap at a second junction, and at least one opening completely through the strap from the outer surface to the inner surface; and where the opening in the third strap is positioned approximately 25% of the distance from the first junction toward the second junction.

15. The method of claim 11, wherein the amplifier and display variables comprise parameter data selected from the group consisting of low frequency filter settings, high frequency filter settings, notch filter settings, amplitude, sensitivity, time base, and montage selection.

* * * * *